United States Patent
Benavitz et al.

(10) Patent No.: US 7,226,469 B2
(45) Date of Patent: Jun. 5, 2007

(54) INSERT MOLDED SUTURE ANCHOR

(75) Inventors: William C. Benavitz, Naples, FL (US); R. Donald Grafton, Naples, FL (US); Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 250 days.

(21) Appl. No.: 10/083,568

(22) Filed: Feb. 27, 2002

(65) Prior Publication Data
US 2002/0087190 A1  Jul. 4, 2002

Related U.S. Application Data

(63) Continuation-in-part of application No. 09/495,816, filed on Feb. 2, 2000, now Pat. No. 6,517,564.

(60) Provisional application No. 60/271,414, filed on Feb. 27, 2001, provisional application No. 60/125,781, filed on Mar. 23, 1999, provisional application No. 60/118,228, filed on Feb. 2, 1999.

(51) Int. Cl.
*A61B 17/04* (2006.01)
*A61B 17/88* (2006.01)

(52) U.S. Cl. ........................... 606/232; 606/72

(58) Field of Classification Search .................. 606/53, 606/60, 72, 73, 144, 148, 228–233
See application file for complete search history.

(56) References Cited

U.S. PATENT DOCUMENTS

| | | | |
|---|---|---|---|
| 2,065,659 A | 12/1936 | Cullen | |
| 4,632,100 A | 12/1986 | Somers et al. | |
| 4,738,255 A | 4/1988 | Goble et al. | |
| 5,100,417 A * | 3/1992 | Cerier et al. | 606/139 |
| 5,102,421 A * | 4/1992 | Anspach, Jr. | 606/232 |
| 5,370,662 A | 12/1994 | Stone et al. | |
| 5,417,651 A | 5/1995 | Guena et al. | |
| 5,417,712 A | 5/1995 | Whittaker et al. | |
| 5,569,306 A * | 10/1996 | Thal | 606/232 |
| 5,578,057 A | 11/1996 | Wenstrom, Jr. | |
| 5,591,207 A * | 1/1997 | Coleman | 606/232 |
| 5,601,557 A | 2/1997 | Hayhurst | |
| 5,643,319 A * | 7/1997 | Green et al. | 606/218 |
| 5,690,677 A * | 11/1997 | Schmieding et al. | 606/232 |
| 5,697,950 A * | 12/1997 | Fucci et al. | 606/232 |
| 5,814,051 A * | 9/1998 | Wenstrom, Jr. | 606/104 |
| 5,827,291 A * | 10/1998 | Fucci et al. | 606/104 |
| 5,964,783 A * | 10/1999 | Grafton et al. | 606/232 |

(Continued)

FOREIGN PATENT DOCUMENTS

EP   632 999   1/1995

(Continued)

*Primary Examiner*—Glenn K. Dawson
(74) *Attorney, Agent, or Firm*—Dickstein Shapiro LLP

(57) ABSTRACT

An insert-molded suture anchor has a biodegradable polymer body molded around a loop of suture. A tapered end disposed on the proximal end of the body is received into a recess in the distal end of a hand driver. Anchoring ribs are formed along the remaining length of the anchor. The suture is held securely within the anchor body during the insert molding process. The anchor is produced by placing the braided suture within an injection mold, and injecting biodegradable polymer into the mold. Using a preferred plication driver, the suture anchor can be utilized for capsular plication procedures.

4 Claims, 3 Drawing Sheets

U.S. PATENT DOCUMENTS

| | | |
|---|---|---|
| 5,993,459 A * | 11/1999 | Larsen et al. ............... 606/104 |
| 6,117,162 A | 9/2000 | Schmieding et al. |
| 6,146,407 A * | 11/2000 | Krebs ......................... 606/232 |
| 6,517,564 B1 | 2/2003 | Grafton et al. |
| 6,554,852 B1 * | 4/2003 | Oberlander ................. 606/232 |
| 6,582,453 B1 * | 6/2003 | Tran et al. .................. 606/232 |
| 6,641,597 B2 * | 11/2003 | Burkhart et al. ............ 606/232 |
| 6,893,448 B2 * | 5/2005 | O'Quinn et al. ............ 606/139 |
| 2004/0106950 A1 * | 6/2004 | Grafton et al. ............. 606/232 |

FOREIGN PATENT DOCUMENTS

| | | | |
|---|---|---|---|
| EP | 0 916 312 A1 * | 5/1999 | ................. 606/232 |
| EP | 0916312 * | 5/1999 | ................. 606/232 |
| GB | 1 602 834 | 11/1981 | |

* cited by examiner

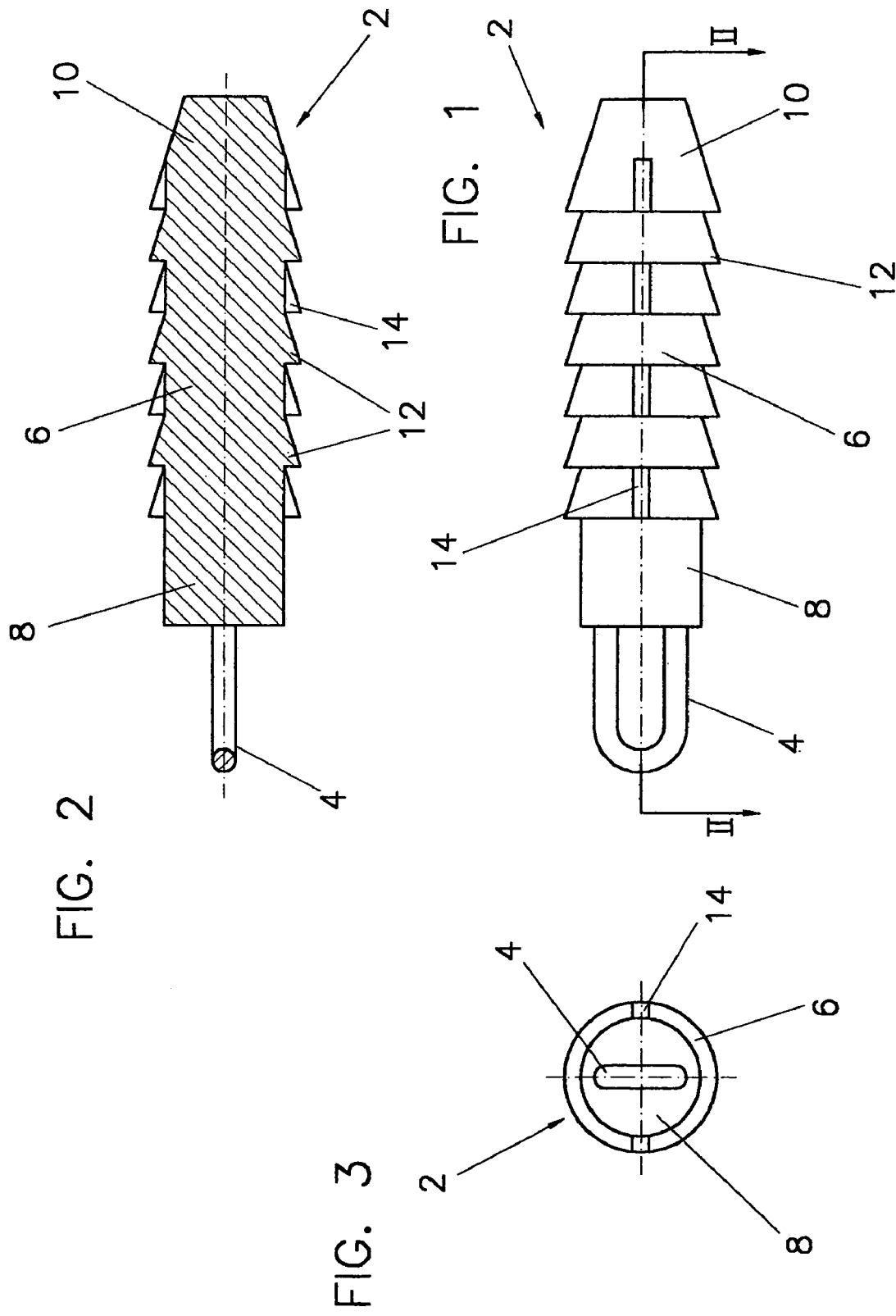

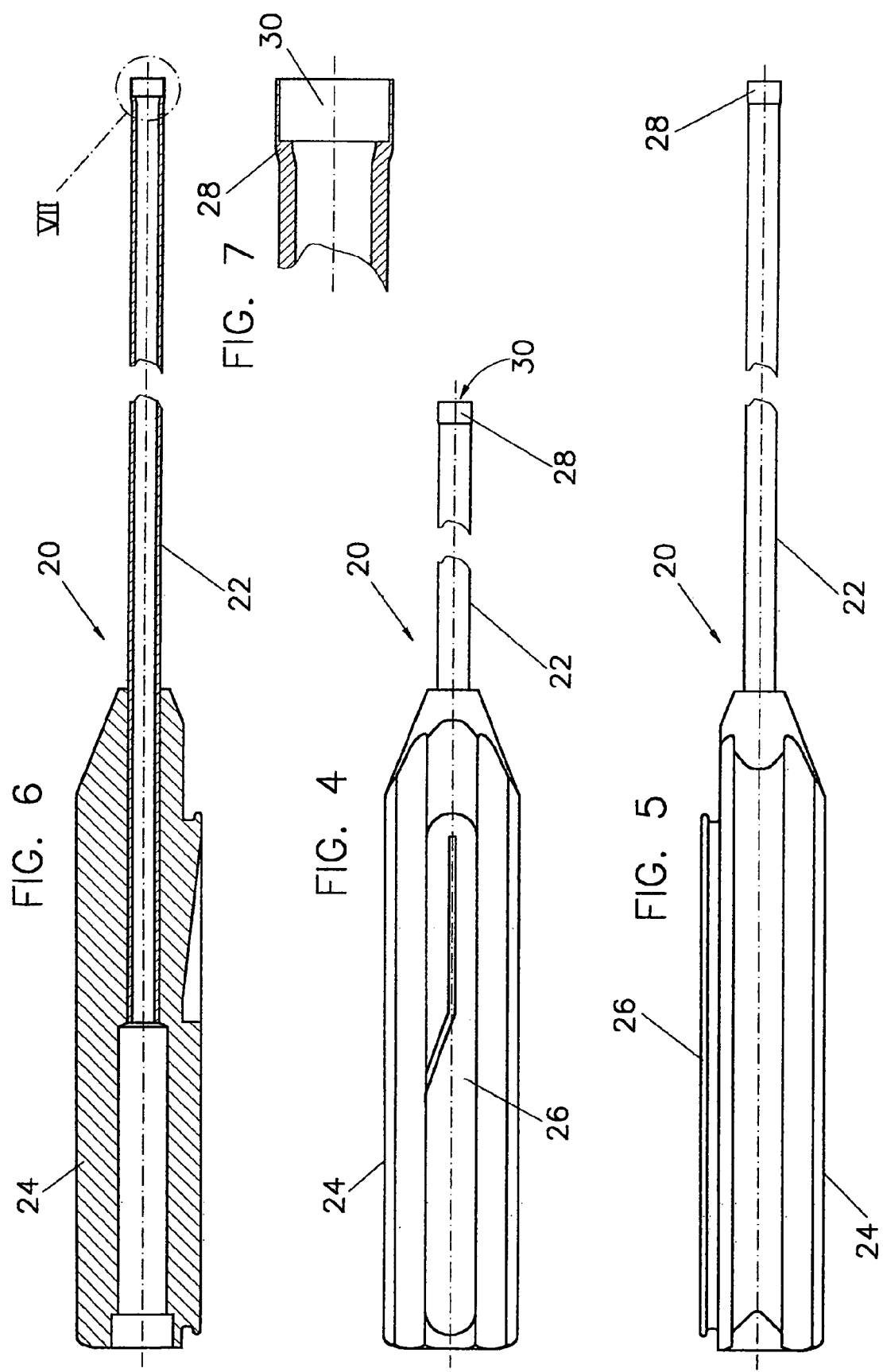

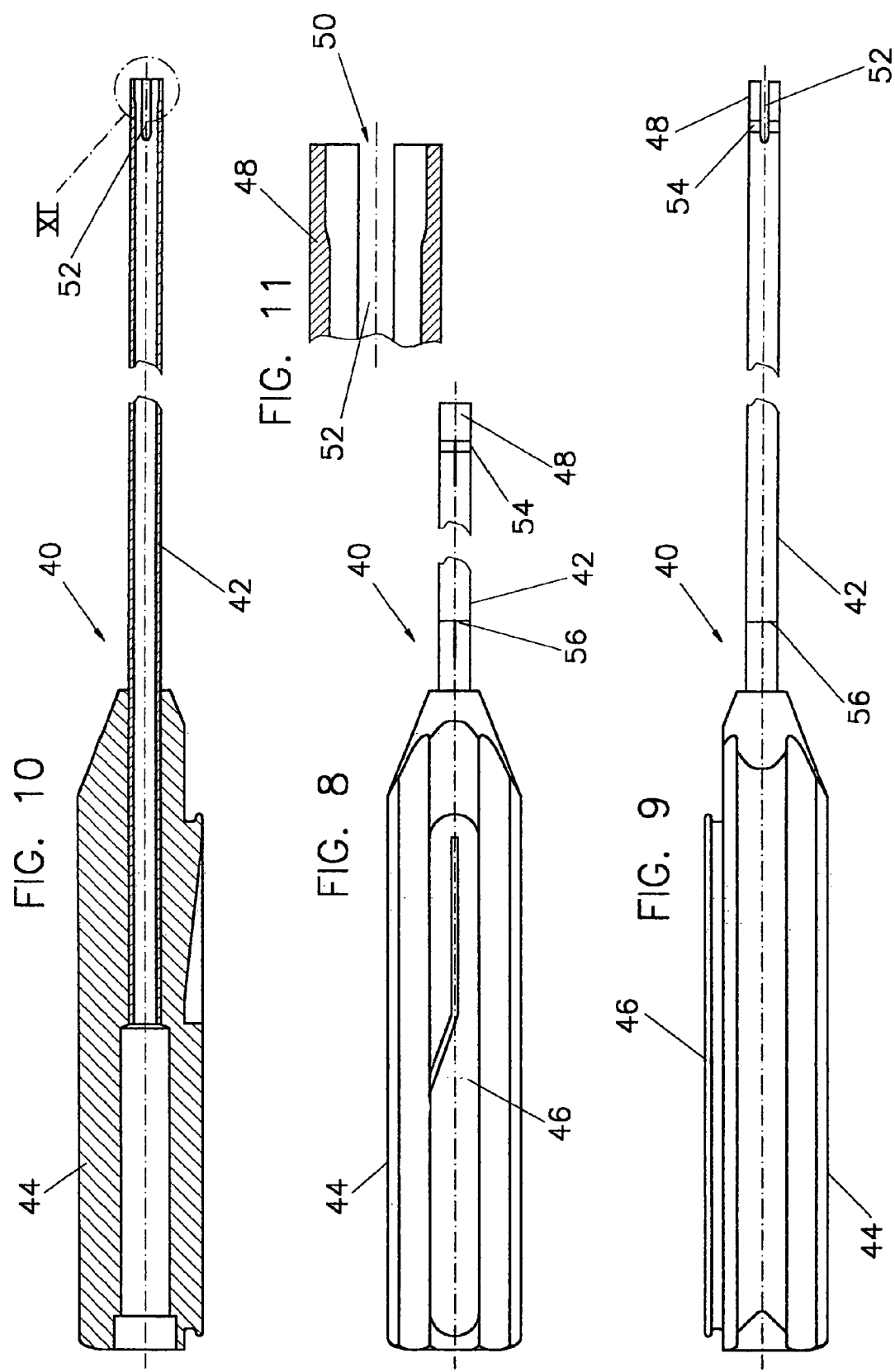

INSERT MOLDED SUTURE ANCHOR

This application is a continuation-in-part of U.S. application Ser. No. 09/495,816, filed Feb. 2, 2000 now U.S. Pat. No. 6,517,564 and claims the benefit of U.S. Provisional Application Ser. No. 60/118,228, filed Feb. 2, 1999 and U.S. Provisional Application Ser. No. 60/125,781, filed Mar. 23, 1999, the disclosures of which are incorporated herein by reference. This application also claims the benefit of U.S. Provisional Application Ser. No. 60/271,414, filed Feb. 27, 2001.

BACKGROUND OF THE INVENTION

1. Field of the Invention

The present invention relates to an apparatus and method for anchoring surgical suture to bone. More specifically, the present invention relates to arthroscopic apparatus and methods for anchoring suture to bone using a suture anchor having suture molded directly into the body of the suture anchor.

2. Description of the Related Art

When soft tissue tears away from bone, reattachment becomes necessary. Various fixation devices, including sutures, screws, staples, wedges, and plugs have been used in the past to secure soft tissue to bone. More recently, various types of threaded suture anchors have been developed.

Suture anchors and implants generally include a structure for attaching or securing the suture to the anchor. U.S. Pat. No. 4,632,100, for example, discloses and claims a threaded suture anchor with a complex press-fitted disc and knot structure which secures the suture to the anchor. In other suture anchors, such as those disclosed in U.S. Pat. No. 5,370,662, the suture is attached to the anchor by passing the suture through an eyelet at the back end of the anchor. Problems can arise if the structure for attaching the suture fails, allowing the suture to become detached from the anchor. Also, in some of the known devices, the suture is exposed to abrasion or cutting by sharp or rough areas along the walls of the bone canal into which the anchor is inserted.

In addition, the eyelet or, in the case of U.S. Pat. No. 4,632,100, the axial opening for receiving the disc to which the suture is knotted, is formed as part of the drive head of the known suture anchors, which weakens the drive head. Various other modifications in the drive head are often employed in connection with suture attachment. For example, recessed grooves may be formed on opposite sides of the drive head to receive and protect the suture from the abrasive areas of the suture anchor tunnel. In such cases, the drive head often is made of a larger diameter to recover the mechanical strength lost from the removal of material relating to the suture-attachment or suture-protection modification.

Accordingly, a need exists for a suture anchor or implant to which suture is secured effectively so as to prevent detachment of the suture. A need also exists for a soft tissue fixation device having a low profile configuration particularly suited for reattachment of tissue to the glenoid rim, for example.

SUMMARY OF THE INVENTION

The suture anchor of the present invention overcomes disadvantages of the prior art, such as those noted above, and achieves the foregoing objectives by providing a push in suture anchor having suture insert-molded into the suture anchor during the manufacturing process.

At least one length of the insert-molded suture extends from the proximal end of the suture anchor body. Both the suture anchor and suture preferably are made with biodegradable materials. According to one embodiment, irregularities are formed along the surface of the suture, especially where it is molded inside the suture body, to increase pullout strength of the suture from the anchor body. The surface irregularities can be formed by various methods including incorporating a thick fiber into the weave of the suture or by tying knots in the suture.

The suture anchor of the present invention has a central body, a distal end, and a proximal end. The body preferably has tapered ribs formed along the distal portion, terminating in a blunt or rounded proximal end. The proximal end of the suture anchor body preferably has a round, tapered drive head which is received in a recess of a hand driver.

The insert-molded suture preferably extends through the entire length of the anchor and exits at the proximal end of the anchor. In a preferred embodiment of the invention, the suture forms a loop outside the proximal end of the anchor. Advantageously, the suture exits the suture anchor along the central axis of the anchor, which prevents suture abrasion by the wall of the bone tunnel into which the anchor is inserted.

Other features and advantages of the present invention will become apparent from the following description of the invention, which refers to the accompanying drawings.

BRIEF DESCRIPTION OF THE DRAWINGS

FIG. 1 is a plan view of the suture anchor of the present invention.

FIG. 2 is a sectional elevation of the suture anchor of FIG. 1.

FIG. 3 is a proximal end view of the suture anchor of FIG. 1.

FIG. 4 is a plan view of a hand driver for inserting the suture anchor of the present invention.

FIG. 5 is an elevation view of the hand driver of FIG. 4.

FIG. 6 is a sectional view of the hand driver of FIG. 4.

FIG. 7 is a detail view of the drive end of the hand driver of FIG. 4.

FIG. 8 is a plan view of an alternative hand driver for a method of capsular plication using the suture anchor according to the present invention.

FIG. 9 is an elevational view of the hand driver of FIG. 8.

FIG. 10 is a sectional elevation of the hand driver of FIG. 8.

FIG. 11 is a detail view of the drive end of the hand driver of FIG. 4.

DETAILED DESCRIPTION OF THE PREFERRED EMBODIMENTS

Referring to FIGS. 1–3, the present invention is shown as a suture anchor 2 having suture 4 that is insert-molded directly into the suture anchor body 6 during the manufacturing process.

The suture anchor body 6 preferably is formed of a bioabsorbable material, poly(l-lactide-co-d,l-lactide) 70:30 (PLDLA) being most preferred. Suture 4 can be any known type of suture selected according to the size of the anchor and the anticipated application. The suture 4 preferably is No. 2 polyester braided suture.

At least one length of the insert-molded suture 4 extends from the proximal end of the suture anchor body. Preferably, the suture extends from the suture anchor body in the form of a loop. Various methods of increasing the pull out strength of the suture from the anchor body are disclosed in U.S. Pat. No. 5,964,783 to Grafton et al. which issued on Oct. 12, 1999 and is assigned to the present applicant, the entire disclosure of which is incorporated herein by reference.

The proximal end 8 of the suture anchor body preferably is tapered for a snug fit into a hand driver described below, for example, with reference to FIGS. 4–7. The distal end 10 of the suture anchor tapers to a blunt tip. Suture anchor 2 is provided with slotted ribs 12 formed circumferentially at least partially around and partially along the length of body 6. Ribs 12 have a truncated, conical shape, each rib increasing in diameter toward the head of the anchor at an angle of preferably 15° with respect to the longitudinal axis of anchor 2, and reaching a major diameter of 3.0 mm. Slots 14 are formed in ribs 12 on alternating sides of body 4.

Referring to FIGS. 4–7, a hand driver 20 according to the present invention is shown. Hand driver 20 includes a cannulated shaft 22 with a cannulated handle 24. A cleat 26 is provided on the handle for securing suture attached to the suture loop on the suture anchor and passed through the cannulated shaft and handle. The distal tip 28 of cannulated shaft 22 provides a recess 30 which receives the proximal end of suture anchor 2. The outer diameter of the distal end of the driver preferably is less than or equal to the maximum outer diameter of the suture anchor.

The suture anchor is inserted into a hole formed in bone. The hole can be formed by punching or boring, for example. The ribs secure the anchor in the bone. The slots enhance attachment in the bone and support bony in-growth for increased pull out strength.

Advantageously, the hole formed in bone is made deep enough, and the suture anchor is advanced into the hole sufficiently, so that the proximal end of the anchor sits flush with or below the bone surface. Accordingly, the repair leaves a smooth bone surface, minimizing or eliminating abrasion or other damage to surrounding soft tissue. The anchor generally becomes encapsulated by fibrous tissue within six weeks after implantation.

Although PLDLA is the most preferred material for the suture anchor of the present invention, other bioabsorbable materials known in the art can be utilized. As used herein, bioabsorbable is considered to be interchangeable with biodegradable, resorbable and absorbable to mean that the device can be at least partially absorbed by the body over time. Preferably, the anchor material is selected so as to absorb or degrade substantially completely within 12–16 months of implantation.

The suture anchor of the present invention is particularly well suited for reattachment of the glenoid labrum or inferior glenohumeral ligament in patients with primary or recurrent anterior dislocation or subluxation of the shoulder in association with adequate post-operative immobilization. More specifically, the anchor also can be used for repair procedures such as capsulabral plication, as described below.

Referring to FIGS. 8–11, a driver 40 for capsule plication using the anchor according to the present invention is shown. Capsulolabral plication is indicated for repair of certain types of shoulder laxity. When pathologically increased anterior laxity is combined with a Bankart lesion, for example, the addition of a capsular plication to the reattachment of the capsulolabral avulsion has been recommended.

Driver 40 includes a cannulated shaft 42 with a cannulated handle 44. A cleat 46 is provided on the handle for securing suture attached to the suture loop on the suture anchor and passed through the cannulated shaft and handle. The distal tip 48 of cannulated shaft 42 provides a recess 50 which receives the proximal end of suture anchor 2. The outer diameter of the distal end of the driver preferably is less than or equal to the maximum outer diameter of the suture anchor. Driver 40 also features a slot 42 which is continuous with recess 50.

The method of capsular plication proceeds using a 36-inch (91.4 cm) long #2 suture to plicate the capsulolabral complex. Both free ends of the suture are brought out an operative cannula. A spear with an included obturator is introduced through a skin incision or a clear cannula. The tip of the spear is positioned on bone and the obturator is removed.

A pilot hole is prepared in bone using either a punch or a drill depending on surgeon preference. With the manual punch, a mallet is used to advance the punch into bone until the punch handle meets the back of the spear and/or the shoulder on the distal part of the punch meets the bone surface. Alternatively, the drill can be attached with a Jacob chuck to a motorized drill and advanced until the stop on the drill bit meets the back of the spear.

After the pilot hole is created and the punch or drill is removed, the sterile-packaged implant 2 is opened to the sterile field using appropriate sterile technique. The implant is removed from the standard hand driver 20 and the suture is unloaded from the implant. A separate sterile packaged plication driver 40 is opened to the sterile field. One of the two legs of the plication suture is selected. This suture leg is the one on the medial side, or the one that passes under the tissue.

The selected suture leg is loaded through the implant eyelet. The implant 2 is positioned on plication driver 40 so that the open side of the eyelet 4 faces the open slot 52 on the driver. The suture leg will exit the slot 52 on the driver 40. The implant with driver is inserted into the prepared pilot hole by hand. A mallet then is used to advance the implant into the hole. The implant is advanced until a second laser line 54 on the distal tip of the driver is flush with the bone surface and a laser line 56 on the proximal part of the implant driver shaft is flush with the back of the spear handle.

The implant driver handle is pulled straight off the implant and the spear is removed. Additional implants are inserted dependent upon the size of the soft tissue defect. Suture passing and knot tying are carried out in the preferred fashion.

Although the present invention has been described in relation to particular embodiments thereof, many other variations and modifications and other uses will become apparent to those skilled in the art.

What is claimed is:

1. A surgical method comprising the steps of:
   loading a suture strand through a flexible eyelet extending from a round, tapered proximal end of an insert molded ribbed, non-threaded suture anchor, the suture anchor comprising a series of truncated cones terminating at its distal end in a truncated cone with a blunt tip, the flexible eyelet comprising a loop of suture, a portion of which has been insert molded into the suture anchor;
   attaching a hand driver to the suture anchor, the driver having a cannulated handle and a cannulated shaft extending from the handle, the cannulated shaft having a recess at a distal end thereof which receives the round, tapered proximal end of the suture anchor, the suture strand loaded through the flexible eyelet of the suture anchor being passed through the cannulated shaft and cannulated handle of the hand driver;

forming a hole in bone;

advancing, without turning, the insert molded ribbed, non-threaded suture anchor into the hole, by pushing the anchor by hand with the driver; and securing tissue to the insert molded ribbed suture anchor by passing the suture strand through the tissue and tying a knot with suture strand to secure the tissue.

2. An insert-molded anchor assembly comprising:

a hand driver having a fully cannulated handle and a cannulated shaft with an open recess on an end of the shaft;

an insert molded ribbed suture anchor comprising an anchor body molded around suture to form a suture loop, the suture loop extending outside the anchor body at the proximal end of the anchor to form a flexible eyelet, the proximal end of the anchor being round and tapered, the round, tapered proximal end of the suture anchor comprising a drive head and being received in the recess on the end of the cannulated shaft of the hand driver, the anchor body comprising a plurality of adjacent truncated cones, the anchor body terminating at its distal end in a truncated cone with a blunt tip; and a suture strand which is loaded through the flexible eyelet of the suture anchor and passes through the cannulated shaft and cannulated handle of the hand driver.

3. The insert-molded anchor assembly of claim 2, wherein the drive head is tapered.

4. A plication driver for a suture anchor, the driver comprising:

a cannulated shaft having a proximal end and a distal end, the distal end of the cannulated shaft having a round cylindrical recess for receiving a round, tapered proximal end of the suture anchor;

a cannulated handle attached to the proximal end of the shaft, the cannulated handle and the cannulated shaft of the driver receiving a suture strand loaded through a flexible eyelet of the suture anchor; and a distally open-ended slot formed as a narrow, elongate opening formed axially through two opposed regions of a wall of the shaft adjacent the recess and opening into the shaft cannula, the slot being continuous with the recess formed in the distal end of the shaft, the slot having a closed end located along the shaft proximal to the recess.

* * * * *